United States Patent [19]
Forbes et al.

[11] Patent Number: 5,668,085
[45] Date of Patent: Sep. 16, 1997

[54] GLYPHOSATE FORMULATIONS COMPRISING ALKOXYLATED AMINE SURFACTANTS

[75] Inventors: James Carnegie Forbes, Chesterfield, Mo.; Michel Maurice Henriet, Noirmont, Belgium; Samuel Hewitt, Chaumont-Gistoux, Belgium; Robert William Mitchell, Overijse, Belgium

[73] Assignee: Monsanto Company, St. Louis, Mo.

[21] Appl. No.: 459,679

[22] Filed: Jun. 2, 1995

Related U.S. Application Data

[63] Continuation of Ser. No. 262,202, Jun. 20, 1994, abandoned, which is a continuation-in-part of Ser. No. 27,612, Jan. 26, 1993, abandoned, which is a continuation of Ser. No. 635,004, Apr. 15, 1991, abandoned, which is a continuation of Ser. No. 184,856, Apr. 22, 1988, abandoned.

[51] Int. Cl.$^6$ .................... A01N 57/02; A01N 25/30
[52] U.S. Cl. .................................................. 504/206
[58] Field of Search ........................................ 504/206

[56] References Cited

U.S. PATENT DOCUMENTS

| | | | |
|---|---|---|---|
| 3,799,758 | 3/1974 | Franz | 71/86 |
| 4,322,239 | 3/1982 | Dutra et al. | 71/86 |
| 4,405,531 | 9/1983 | Franz | 548/579 |
| 4,413,125 | 11/1983 | Gaertner | 546/22 |
| 4,440,562 | 4/1984 | Prill | 71/86 |
| 4,447,255 | 5/1984 | Schott et al. | 71/86 |
| 4,528,023 | 7/1985 | Ahle | 71/86 |
| 4,612,034 | 9/1986 | Kruger et al. | 71/86 |

FOREIGN PATENT DOCUMENTS 131437  10/1986  Poland.

OTHER PUBLICATIONS

J. Wade Van Valkenburg *Adjuvants for Herbicides* (1982) "Terminology, Classification, and Chemistry" pp. 1–9.
McCutcheon's *Emulsifiers & Detergents* (1982 Int'l Edition) pp. 81, 87, 261–283.

*The Pesticide Manual* 9th Edition, British Crop Protection Council, pp. 459–460 1991.

(List continued on next page.)

*Primary Examiner*—S. Mark Clardy
*Attorney, Agent, or Firm*—Stanley M. Tarter; Arnold, White & Durkee

[57] ABSTRACT

Aqueous concentrates containing glyphosate herbicide which on dilution give spray solutions having higher herbicidal unit activity than prior art solutions comprise:

(a) solubilized glyphosate equivalent to at least 40 grams per liter of glyphosate acid;

(b) a surfactant which is (i) an amine having the formula

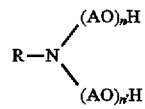

where R represents a straight- or branched-chain alkyl or alkenyl group having from about 8 to about 22 carbon atoms, A represents an alkylene group, for example an ethylene or propylene group, and n and n' are integers such that n+n' has a value of from about 2 to about 8, (ii) a mixture of such amines having different groups R, the average number of carbon atoms in the groups R being from about 8 to about 22, or (iii) a mixture of such amines having different values of n and n', n and n' being integers such that in the mixture the average value of n+n' is from about 2 to about 8, R having a single value or an average value as in a mixture (ii);

and optionally (c) an agriculturally acceptable inorganic ammonium salt;

wherein the weight ratio of (a) expressed as glyphosate acid equivalent to (b) is from about 1:1.75 to about 6:1;

and wherein the weight ratio of (c) to (a) expressed as glyphosate acid equivalent is at most about 3.6:1.

21 Claims, 11 Drawing Sheets

OTHER PUBLICATIONS

*Advanced Organic Chemistry*, (1961) Fieser & Fieser, Reinhold Publishing Corp, pp. 982–985 & 990.

*Chemical Abstract*, vol. 102 (1985) Abstract #127180p.

Turner, D. J. "The Effects of Additives on the Control of Agropyron Repens with Glyphosate" *Proceedings of the Conference on Grass Weeds in Cereals in the U.K.* (1981) pp. 167–175.

Wyrill, J.B., et al. "Glyphosate Toxicity . . . as Influenced by Surfactants." *Weed Science* 25(3):275–287. May 1977.

Turner, D.J., et al. "Effect of Ammonium Sulfate and Other Additives Upon the Phytotoxicity of Glyphosate . . ." *Weed Research* 20:139–146. 1980.

Turner, D.J. et al "Studies with Alternative Glyphosate Formulations" BCPC Monogram No. 28. 1985. pp. 135–145.

Turner, "Effect on Glyphosate Performance of Formulation, Additives, and Mixing with Other Herbicides," Ch. 15 of *The Herbicide Glyphosate*, Butterworths, ed. 1985.

GLYPHOSATE FORMULATIONS COMPRISING ALKOXYLATED AMINE SURFACTANTS

REFERENCE TO RELATED APPLICATION

This application is a continuation of U.S. Ser. No. 08/262,202 filed Jun. 20, 1994 (now abandoned), which is a continuation-in-part of U.S. Ser. No. 08/027,612 filed Jan. 26, 1993 (now abandoned), which is a continuation of U.S. Ser. No. 07/635,004 filed Apr. 15, 1991 (now abandoned), which is a continuation of U.S. Ser. No. 07/184,856 filed Apr. 22, 1988 (now abandoned).

BACKGROUND OF THE INVENTION

This invention relates to improved glyphosate formulations.

Glyphosate (N-phosphonomethylglycine) is well known as a foliage acting herbicide. In the free acid form, glyphosate has low water solubility, and because of this, commercial formulations contain a water-soluble salt of glyphosate. For example, in Roundup® herbicide, glyphosate is present as the water-soluble mono-isopropylamine salt.

Several studies on the effect of surfactants on the herbicidal activity of the monoisopropylamine salt of glyphosate are reported in the literature. For example, Turner and Loader, Weed Research, 1980, Vol 20, 139–146 reported that fatty amine ethoxylates having a hydrophile-lipophile balance of 17, are generally the most effective in increasing the herbicidal activity of solutions of Roundup® herbicide. In the same publication, the authors state that with spray solutions containing ammonium sulfate, responses to surfactants were different, with lipophilic surfactants, for example fatty amine ethoxylates having a hydrophile-lipophile balance of 6, usually having greater effects.

In 1985 BCPC Monogram No. 28 Symposium on Application and Biology "Studies with Alternative Glyphosate Formulations", Turner and Tabbush describe the results of some trials with glyphosate acid formulated as a foliage spray. In summarizing the results, they state that glyphosate acid had relatively little activity unless surfactants and/or ammonium sulfate was added, but that when this was done, its phytotoxicity was equivalent to that of Roundup® herbicide. There is an observation that glyphosate acid is much more soluble in a solution of a tertiary amine from tallow containing 15 mols of ethylene oxide per mol of amine than in pure water.

U.S. Pat. No. 4,612,034 describes herbicidal formulations comprising mixtures of the isopropylamine salt of glyphosate and a potentiating amount of a specified class of thiocyanates including ammonium thiocyanate.

In the experiments described in 1985 BCPC Monogram No. 28 on the preparation of salts of glyphosate or the solubilization of glyphosate acid with ethoxylated fatty acid amines, the ethoxylated fatty acid amine surfactant was used in an excess of at least five parts by weight per part by weight of glyphosate acid. While one experiment described in Weed Research, 1980, Vol 20, 139–146, uses a solution containing less surfactant than glyphosate (as Roundup® herbicide, which itself contains a significant amount of surfactant) it was applied by a controlled drop technique at 20 l/ha. For experiments in which solutions were sprayed by conventional techniques at normal farm application rates of about 200 l/ha, however, the solutions contained about twice as much surfactant as glyphosate.

In 1981 D. J. Turner in the Proceedings of the Conference on Grass Weeds in Cereals in the United Kingdom Conference presented a reading entitled "The Effect of Additives on the Control of Agropyron Pepens with Glyphosate". He reported the effect of using mixtures of ammonium sulfate and Ethomeen C/12 surfactant which is an ethoxylated derivative of cocoamine containing an average of about 2 ethoxy groups. Turner's compositions contained a large amount of ammonium sulfate in relation to the amount of glyphosate. The lowest ratio of ammonium sulfate to glyphosate tested by Turner has been calculated to be 3.75:1. At the high ratios of ammonium sulfate to glyphosate disclosed by Turner it becomes impractical to formulate aqueous solutions of glyphosate salt, surfactant and ammonium sulfate except at glyphosate acid equivalent (a.e.) concentrations below about 90 g/l. Turner's compositions cannot therefore be formulated as aqueous concentrates at a glyphosate loading which is high enough to be commercially attractive in most agricultural markets.

In the investigations leading to the present invention, we worked at conventional spray rates (around 200 l/ha), and with solutions containing lower surfactant to glyphosate ratios and/or lower ammonium sulfate to glyphosate ratios than those disclosed in the prior art for solutions sprayed at those rates. We have found that with our solutions, better results are obtained under most conditions with the lipophilic fatty amine ethoxylates than with the more hydrophilic fatty amine ethoxylates hitherto thought to be optimum. This is so, whether or not the solution also contains ammonium sulfate. These observations are surprising in view of the prior art which suggests that the lipophilic surfactants would not be the surfactants of choice except in the presence of rather high amounts of ammonium sulfate.

Nowhere in the prior art has it been discovered that, at low surfactant to glyphosate (a.e.) ratios (about 1.75:1 or lower), aqueous formulations of glyphosate with an alkoxylated amine surfactant having about 8 or fewer alkoxy groups, either substantially free of inorganic ammonium salt or with a ratio of such salt to glyphosate (a.e.) lower than about 3.6:1, provide better performance than otherwise similar formulations, hitherto taught to be optimal, with an alkoxylated amine surfactant having about 15 alkoxy groups. The present invention unexpectedly provides aqueous concentrate glyphosate formulations with significantly enhanced herbicidal activity over prior art formulations. What is particularly surprising is that the class of surfactants used at low surfactant to glyphosate ratios in compositions of the invention is taught by the prior art (see the Turner references cited above and also Wyrill and Burnside, Weed Science Vol. 25 (1977), pp. 275–287) to be of relatively poor efficacy when tested at high surfactant to glyphosate ratios.

A feature of the present invention is that the amount of alkoxylated amine surfactant relative to total glyphosate can be reduced significantly below the ratio disclosed in the prior art for conventional spray solutions having no or low amounts of inorganic ammonium salt, while enhancing the herbicidal activity per unit of glyphosate by comparison with similar (prior art) solutions in which the alkoxylated amine surfactant has about 15 alkoxy groups instead of about 8 or fewer in solutions of the invention.

SUMMARY OF THE INVENTION

This invention provides a composition comprising an aqueous solution containing (a) solubilized glyphosate equivalent to at least 40 g/l of glyphosate acid; and (b) a surfactant which is (i) an amine having the formula

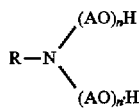

where R represents a straight- or branched-chain alkyl or alkenyl group having from about 8 to about 22 carbon atoms, A represents an alkylene group, for example an ethylene or propylene group, and n and n' are integers such that n+n' has a value of about 2 to about 8, (ii) a mixture of such amines having different groups R, the average number of carbon atoms in the groups R being from about 8 to about 22, or (iii) a mixture of such amines having different values of n and n', n and n' being integers such that the average value of n+n' in the mixture is about 2 to about 8, R having a single value or an average value as in a mixture (ii);

and wherein the weight ratio of (a) expressed as glyphosate a.e. to (b) is from about 1:1.75 to about 6:1. The composition may optionally contain an agriculturally acceptable inorganic ammonium salt, for example ammonium sulfate, with the proviso that the weight ratio of said ammonium salt to glyphosate a.e. is at most about 3.6:1.

Also provided is a herbicidal method comprising spraying, at a volume in the range from about 100 to about 400 l/ha, a solution comprising solubilized glyphosate and surfactant as defined above, optionally with an agriculturally acceptable ammonium salt, in a weight ratio of glyphosate a.e. to surfactant of from about 1:1.75 to about 6:1 and a weight ratio of said ammonium salt to glyphosate a.e. of about 3.6:1 at most, such a method giving superior herbicidal efficacy by comparison with spraying an otherwise similar solution in which the surfactant is replaced by an ethoxylated tallowamine surfactant having an average of about 15 ethoxy groups.

DETAILED DESCRIPTION OF THE INVENTION

Figure 1:
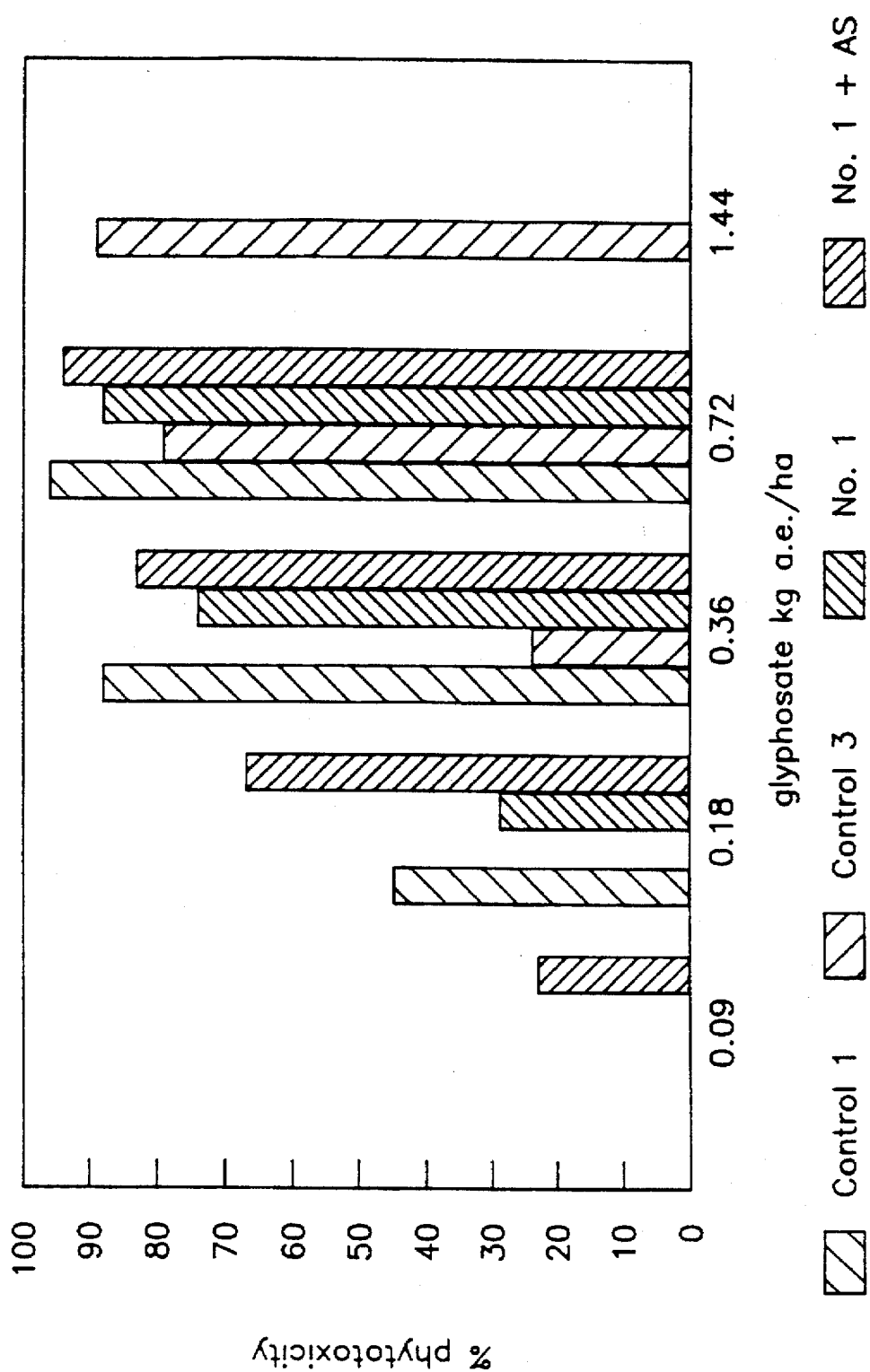
FIG. 1 shows results obtained in growth room tests on wheat.

Novel aqueous concentrate compositions of high herbicidal efficacy are provided comprising (a) solubilized glyphosate equivalent to at least 40 g/l of glyphosate acid; and (b) a surfactant which is (i) an amine having the formula

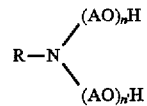

where R represents a straight- or branched-chain alkyl or alkenyl group having from about 8 to about 22 carbon atoms, A represents an alkylene group, for example an ethylene or propylene group, and n and n' are integers such that n+n' has a value of about 2 to about 8, (ii) a mixture of such amines having different groups R, the average number of carbon atoms in the groups R being from about 8 to about 22, or (iii) a mixture of such amines having different values of n and n', n and n' being integers such that the average value of n+n' in the mixture is about 2 to about 8, R having a single value or an average value as in a mixture (ii);

and wherein the weight ratio of (a) expressed as glyphosate a.e. to (b) is from about 1:1.75 to about 6:1. Composition of the invention may optionally further comprise an agriculturally acceptable inorganic ammonium salt, but if so, in relatively small amounts such that the weight ratio of inorganic ammonium salt to glyphosate a.e. is about 3.6:1 at most.

A further aspect of the invention is a spray solution intended for spraying at conventional volume rates (about 100 to about 400 l/ha) and containing solubilized glyphosate and surfactant as defined above in a weight ratio of glyphosate a.e. to surfactant of from about 1:1.75 to about 6:1. Spray solutions of the invention may optionally contain an agriculturally acceptable inorganic ammonium salt, if so, again, at a weight ratio of about 3.6:1 at most with glyphosate a.e. A herbicidal method comprises spraying weeds with the said spray solution at about 100 to about 400 l/ha, the concentration of (a) in the spray solution being such that the application rate of glyphosate a.e. is from about 0.125 to about 1.5 kg/ha.

In the compositions of the invention, glyphosate is solubilized by the presence in the solution of one or more agriculturally-acceptable cations. Such cations include the cationic forms of the alkoxylated amine surfactants, alkali metal cations, for instance sodium and potassium, and ammonium and substituted ammonium cations. The latter include cations derived from primary or secondary amines such as isopropylamine or dimethylamine and from diamines such as ethylenediamine. Other examples of agriculturally acceptable salts of glyphosate are aminoguanidine salts and trialkyl-sulfonium salts, for example the trimethylsulfonium salt, as disclosed respectively in EP-A-0 088 180 and U.S. Pat. No. 4,405,531.

Formulations containing (a) and (b) in ratios towards the lower (1:1.75) end of the range stated above can be prepared from low molecular weight surfactants by the solubilization of glyphosate acid with the surfactant alone. In most embodiments however, the upper limitation on the amount of surfactant requires the solution to contain other agriculturally acceptable cations in addition to the surfactant cations. In these embodiments, the solubilized glyphosate can be derived (i) partly from glyphosate acid solubilized by means of the surfactant and partly from a salt of glyphosate with another agriculturally-acceptable cation, or (ii) wholly from a salt of glyphosate with such another agriculturally-acceptable cation.

As discussed above, the concentrates of the invention may optionally contain a significant amount of an agriculturally acceptable inorganic ammonium salt in addition to components (a) and (b). Concentrates containing no significant amount of such salt may contain up to about 450 g/l, for example from 150 to 450 g/l or even more, of glyphosate a.e. at ambient temperatures, depending on the water-solubility of the glyphosate salt. For example, when the glyphosate salt is the monoisopropylamine salt, solutions containing 250–400 g/l of glyphosate acid equivalent are easily prepared. Monoammonium glyphosate shows similar solubility characteristics but certain alkali metal salts, for example the potassium salt, are somewhat less soluble. In such cases, the maximum concentration of solubilized glyphosate obtainable, expressed as a.e., is perhaps 250–300 g/l.

When an inorganic ammonium salt is present, the maximum loading of solubilized glyphosate is inevitably reduced. The higher the ammonium salt concentration, the lower is the glyphosate concentration attainable. For this reason, formulations of the invention have an upper limit of ammonium salt to glyphosate a.e. weight ratio of about 3.6:1. Lower ammonium salt to glyphosate a.e. weight ratios, for example from about 2:1 to about 3:1, are preferred. It is stressed, however, that inorganic ammonium salt is optional as a constituent of the formulation described and claimed herein. Even in the total absence of such salt, formulations of the invention are shown herein to provide significantly superior herbicidal efficacy by comparison with otherwise similar prior art formulations in which the surfactant is an ethoxylated tallowamine having an average of about 15 ethoxy groups.

In general, on economic grounds, concentrates of the invention containing a minimum of water, i.e. solutions that are substantially saturated, are preferred. Depending on the climatic conditions to which the solutions are likely to be subjected between manufacture and use, they can be made so that they are saturated at, for example, −5° C., 0° C. or +10° C. Normally a safety margin will be provided, so that a solution which would not be expected to experience temperatures below 10° C., for instance, would nevertheless be stable (i.e. not deposit solids) at, for instance, 5° C. In addition, the concentrates of the invention can contain conventional anti-freeze additives such as ethylene glycol, polyethylene glycols or glycerol.

In compositions of the invention, the maximum amount of surfactant is determined mainly by economic considerations. Higher levels of surfactant may increase the unit herbicidal effect of the glyphosate, but these are not cost-effective beyond a certain level. When the concentrates are viewed as precursors of spray solutions which also contain an agriculturally acceptable inorganic ammonium salt, there is little advantage in using more surfactant than about 1.5 parts per part by weight of glyphosate a.e. At the other end of the range, the maximum preferred glyphosate a.e. to surfactant weight ratio is about 4:1. More preferred ranges of ratios are from 1:1 to about 3:1, although the limits can vary depending on the particular surfactant used, the species of weeds to be controlled and other factors.

Commercially available amine surfactants within the above formula are often mixtures rather than single compounds. They include alkoxylated derivatives of "cocoamine" in which the groups R correspond to alkyl groups derived from various fatty acids including myristic, lauric, palmitic and stearic acids. The average number of carbon atoms in R in cocoamine is 12–14. Other examples are alkoxylated derivatives of "oleylamine", where the principal carbon chain of R corresponds to that of oleic acid (18 carbon atoms), and of "tallowamine" where R is mainly a mixture of hexadecyl and octadecyl. Such commercial surfactants are also usually mixtures of molecules having various values of n+n', and surfactants having a low average value of n+n' may contain a minor proportion of non-alkoxylated or mono-alkoxylated amines. The preferred alkoxylated derivatives are the ethoxylated derivatives.

In general, lower molecular weight surfactants are preferred to higher molecular weight surfactants, because a given weight of the former provides a higher molecular concentration of surfactant than the same weight of the latter. The most preferred surfactants are those where A represents an ethylene group, and those where the number or average number of carbon atoms in the group or groups R is from about 10 to about 20. As regards the value or average value of n+n', in preferred surfactants this lies in the range from about 1.5 to about 12, more especially in the range from about 2 to about 10. Specific examples of preferred surfactants are ethoxylated derivatives of cocoamine, tallowamine and oleylamine where in each case n+n' has an average value of about 2, about 5 or about 8.

For the preparation of concentrates of the invention where the cationic form of the surfactant is at least partially responsible for the solubility of the glyphosate, a solution of solubilized glyphosate acid can in many instances be made simply by mixing the acid and the alkoxylated amine surfactant in an aqueous medium at room temperature or slightly above. A clear solution is obtained within a few minutes. The amount of surfactant required to solubilize the glyphosate acid is normally about 1:1 molar equivalent amount. However, slightly less, for example 90% of the molar equivalent amount, may be sufficient in certain instances, while in others it may be preferable to use a small excess, for instance up to 30% molar excess of the surfactant. Considerations determining the maximum amount of surfactant employed are discussed above. Where it is necessary to provide part of the glyphosate in the form of a salt of glyphosate with another agriculturally-acceptable cation, the solubilized glyphosate acid solution is then mixed with a solution of the glyphosate salt in the proportions to provide the required amounts of each component in the final concentrate. Concentrates of the invention where a cation other than the cationic form of the surfactant is present in sufficient amount alone to solubilize the glyphosate can be prepared by simply mixing the components at room temperature. The surfactants are normally viscous materials which slowly dissolve when stirred with an aqueous solution of the glyphosate salt. Also, if required, a solution of an agriculturally-acceptable ammonium salt can be incorporated at this stage. In general, the solutions employed throughout will be relatively concentrated or even substantially saturated, to minimize the amount of water in the concentrate. If necessary, however, some adjustment in this respect can be made after mixing, by evaporation or addition of water.

Examples of agriculturally acceptable inorganic ammonium salts known to be effective in enhancing the herbicidal effect of glyphosate and other water-soluble or water-solubilizable herbicides include ammonium sulfate, ammonium nitrate, ammonium phosphate, ammonium sulfamate and ammonium thiocyanate. Of these ammonium sulfate is generally preferred.

In concentrates that contain ammonium salt, the amount so included will depend on its solubility in the presence of the other components. To achieve a given level of ammonium salt, however, adjustments in the amounts of the other components can be made. Generally, the amount will be at least about 0.5 parts, for example from about 1 to about 3.6 parts, by weight of ammonium salt per part by weight of component (a), expressed as a.e. These concentrates typically contain at least about 70 g/l, for example from about 80 to about 150 g/l of component (a) and from about 100 to about 350 g/l of ammonium salt, and the weight ratio of component (a) expressed as a.e. to component (b) typically falls in the range from about 2:1 to about 1:1.75.

An example of a specific composition is as follows:

| | |
|---|---|
| Glyphosate acid | 74 g/l |
| Glyphosate monoisopropylamine salt (expressed as acid equivalent) | 49 g/l |
| C 2* surfactant | 120 g/l |
| Ammonium sulfate | 280 g/l |

*An ethoxylated derivative of cocoamine containing an average of about 2 ethoxy groups.

A preferred class of concentrates containing an ammonium salt are compositions which contain 80 to 130 g a.e./l of component (a), present as the monoisopropylamine salt of glyphosate, 100 to 180 g/l of component (b), component (b) being an ethoxylated cocoamine derivative with n+n' having an average value of about 2, and from 260 to 320 g/l of ammonium sulfate.

A preferred class of concentrates which are substantially free of inorganic ammonium salt are compositions which contain 340 to 420 g a.e./l of component (a), present as the monoisopropylamine salt of glyphosate, and, as component (b), an ethoxylated cocoamine derivative with n+n' having an average value of about 2, wherein the weight ratio of (a) expressed as a.e. to (b) is about 2:1.

The present invention includes a herbicidal spray solution for spraying at conventional volume rates, which comprises (a) a solubilized glyphosate component, said glyphosate being present (i) partly as glyphosate acid solubilized by means of a surfactant as defined above and partly as a salt of glyphosate with another agriculturally acceptable cation, (ii) wholly as glyphosate acid solubilized by means of a said surfactant, or (iii) wholly as a salt of glyphosate with an agriculturally acceptable cation other than the cationic form of the surfactant, and (b) a surfactant as defined above, the weight ratio of (a) expressed as a.e. to (b) being from about 1:1.75 to about 6:1.

The concentration of glyphosate in the spray solution will typically be such that when sprayed at about 100 to about 400 l/ha, the application rate of glyphosate a.e. is from about 0.125 to about 1.5 kg/ha.

Optionally, such a spray solution also contains a water soluble, agriculturally acceptable inorganic ammonium salt. The amount of the inorganic ammonium salt used can vary according to the weeds to be treated, the available spray equipment, climatic conditions, etc. Typically, however, the solution will be sprayed at about 100 to about 400 l/ha, and at a dosage rate of at least 0.125 kg/ha glyphosate a.e., and the solution will contain at least the same weight concentration of ammonium salt as glyphosate acid equivalent. For example, the weight ratio of glyphosate acid to ammonium salt in the solution can range from 1:1 to 1:3.6.

A preferred method for preparing a herbicidal spray solution as described above is to mix a concentrate of the invention with water and optionally with an ammonium salt if such salt is not included in the concentrate, but if desired, the individual components of the solution can be mixed in a spray tank with the required volume of water.

The concentrates and solutions of the invention may contain optional additional components. As indicated above, these include anti-freeze agents. Other examples are dyes, thickening agents, anti-foam agents, for instance silicone-based anti-foam agents, and secondary surfactants, for instance non-ionic surfactants such as polyoxyethylene ethers or esters. The concentrates and solutions of the invention may also be mixed with other water soluble herbicides, for example but not limited to, salts of 2,4-dichlorophenoxyacetic acid or of 4-chloro-2-methylphenoxyacetic acid, or with finely-divided water soluble herbicides, for example but not limited to, triazines or substituted ureas.

The invention is illustrated by the following examples, it being understood that the invention is not limited thereto.

Tables 1 to 3 show solutions of the invention where solubilization of glyphosate acid relies at least in part on the presence of the cationic form of the surfactant. These solutions were prepared by first solubilizing glyphosate acid (crystals containing 9% by weight of water) by stirring in water at room temperature or at a temperature not exceeding 60° C., with about 1.05 molar equivalents of ethoxylated amine surfactant per mole of glyphosate acid. When required, the solution thus obtained was then mixed with a solution of a mono salt (ammonium, isopropylamine or potassium) of glyphosate and, if required, water, to give solutions having concentrations and ratios of glyphosate a.e. to surfactant shown in the Tables below.

In the Tables, which show the percentages by weight of the various components, the surfactants are identified by the initial letter of the amine and by the average number of ethoxy groups. Thus C 2 indicates a surfactant derived from cocoamine and having an average of about 2 ethoxy groups; O5 indicates a surfactant derived from oleylamine and having an average of about 5 ethoxy groups; S 8 indicates a surfactant derived from stearylamine and having an average of about 8 ethoxy groups; T 10 indicates a surfactant derived from tallowamine and having an average of about 10 ethoxy groups, etc. Glyphosate salts are identified as AM (ammonium), IP (isopropylamine) or K (potassium).

The solutions of Table 1 contain approximately 300 g/l of glyphosate a.e. and 150 g/l of surfactant. The latter corresponds to 13.64% by weight of surfactant in the solution. The glyphosate salt is the monoisopropylamine salt. Solutions 10 and 11 contain ethoxylated amine surfactants having more than 8 ethoxy groups; the surfactant of Solution 11 is well known in prior art. These two solutions are included here as reference examples.

TABLE 1

| Solution No. | 91% glyphosate acid (%) | Surfactant | Glyphosate salt (%) |
|---|---|---|---|
| 1 | 8.92 | C2 | 41.69 |
| 2 | 6.09 | C5 | 47.30 |
| 3 | 4.62 | C8 | 50.20 |
| 4 | 7.22 | O2 | 45.06 |
| 5 | 5.25 | O5 | 48.97 |
| 6 | 4.12 | O8 | 51.20 |
| 7 | 4.15 | S8 | 51.14 |
| 8 | 5.30 | T5 | 48.86 |
| 9 | 4.15 | T8 | 51.14 |
| 10 | 3.63 | T10 | 52.17 |
| 11 | 2.76 | T15 | 53.90 |

Table 2 gives the percent by weight of components in a series of solutions containing glyphosate acid, the monoisopropylamine salt of glyphosate and an ethoxylated amine surfactant, and having different weight ratios of glyphosate a.e. to surfactant.

TABLE 2

| Solution No. | 91% Glyph acid (%) | Glyph salt (%) | Surfactant (%) | Code | Glyph a.e. to surfactant ratio | Glyph a.e. g/l |
|---|---|---|---|---|---|---|
| 12 | 8.92 | 12.02 | 13.64 | C2 | 1:1 | 145 |
| 13 | 5.10 | 57.74 | 7.80 | C2 | 4:1 | 360 |
| 14 | 4.85 | 21.51 | 14.29 | C8 | 1:1 | 154 |
| 15 | 2.77 | 65.75 | 8.18 | C8 | 4:1 | 383 |
| 16 | 7.67 | 15.91 | 14.29 | T2 | 1:1 | 151 |
| 17 | 7.32 | 44.86 | 13.64 | T2 | 2:1 | 300 |
| 18 | 4.39 | 62.55 | 8.18 | T2 | 4:1 | 379 |

Table 3 gives the percent by weight of components in solutions where the glyphosate salt is the ammonium (AM) or potassium (K) salt. In all solutions the weight ratio of glyphosate a.e. to surfactant is 2:1. Solutions 21, 22, 25 and 26 contain ethoxylated amine surfactants having more than 8 ethoxy groups and are included here as reference examples.

TABLE 3

| Solution No. | 91% Glyphosate acid (%) | Glyphosate salt (%) | Code | Surfactant (%) | Code |
|---|---|---|---|---|---|
| 19 | 8.92 | 67.04 | K | 13.64 | C2 |
| 20 | 8.92 | 60.23 | AM | 13.64 | C2 |
| 21 | 3.73 | 77.25 | K | 12.73 | C10 |
| 22 | 3.98 | 74.36 | AM | 13.64 | C10 |
| 23 | 7.32 | 72.13 | K | 13.64 | T2 |
| 24 | 7.32 | 64.81 | AM | 13.64 | T2 |
| 25 | 3.39 | 78.30 | K | 12.73 | T10 |
| 26 | 3.63 | 75.37 | AM | 13.64 | T10 |

Solutions 21 and 25 contained approximately 280 g/l and 140 g/l of glyphosate a.e. and surfactant respectively. In the other solutions, the corresponding figures are 300 g/l and 150 g/l.

Table 4 shows compositions of the invention which were prepared by stirring a 62% by weight aqueous solution of the monoisopropylamine salt of glyphosate at room temperature with the required amount of surfactant, and, then, if required, with a saturated solution of ammonium sulfate. Solutions 32 and 34 contain ethoxylated amine surfactants having more than 8 ethoxy groups and are included as reference examples.

TABLE 4

| Solution No. | Surfactant Code - g/l | Glyphosate (a.e) g/l | Ammonium Sulfate g/l | Weight Ratio Glyphosate a.e. to surfactant |
|---|---|---|---|---|
| 27 | C 2 - 180 | 360 | — | 2:1 |
| 28 | C 2 - 200 | 400 | — | 2:1 |
| 29 | C 2 - 120 | 120 | 280 | 1:1 |
| 30 | C 2 - 140 | 90 | 300 | 1:1.56 |
| 31 | C 5 - 202 | 404 | — | 2:1 |
| 32 | C 10 - 204 | 407 | — | 2:1 |
| 33 | O 8 - 203 | 405 | — | 2:1 |
| 34 | S 10 - 203 | 406 | — | 2:1 |
| 35 | T 5 - 201 | 402 | — | 2:1 |
| 36 | C 2 - 220 | 120 | — | 1:1.75 |
| 37 | C 2 - 150 | 150 | — | 1:1 |
| 38 | C 2 - 100 | 399 | — | 4:1 |
| 39 | C 2 - 59 | 356 | — | 6:1 |
| 40 | C 2 - 100 | 100 | 320 | 1:1 |

TABLE 4-continued

| Solution No. | Surfactant Code - g/l | Glyphosate (a.e) g/l | Ammonium Sulfate g/l | Weight Ratio Glyphosate a.e. to surfactant |
|---|---|---|---|---|
| 41 | C 2 - 120 | 100 | 300 | 1:1.2 |
| 42 | C 2 - 180 | 110 | 260 | 1:1.64 |
| 43 | C 2 - 120 | 120 | 260 | 1:1 |
| 44 | C 2 - 100 | 130 | 260 | 1.3:1 |

In Table 4 above Solution 29 has a weight ratio of ammonium sulfate to glyphosate a.e. of 2.3:1. Solutions 30 and 41 have weight ratios of ammonium sulfate to glyphosate a.e. of 3.3:1 and 3:1, respectively. Solutions 40, 42, 43 and 44 have weight ratios of 3.2:1, 2.4:1, 2.2:1 and 2:1, respectively.

Growth room herbicidal evaluations were carried out using the following procedure. Plants were grown from seed in 13 cm pots containing a natural sandy loam soil. All irrigation was supplied automatically from below, mineral nutrients being added to the irrigation supply as required. The pots were placed in Conviron growth rooms with a 14 hour photoperiod, illuminance of 600 micro einsteins $m^{-2}s^{-1}$ and a temperature regime of 15° C. (day), 9° C. (night). About two weeks before spraying, (2–4 weeks after sowing) plants were thinned by hand to leave a uniform stand.

At least one week before treatment, the plants were moved to a larger growth room with precise relative humidity as well as temperature control; the RH regime employed was 50% (day), and 65% or 75% (night). Plants remained in this room for the remainder of the experiment. Before spraying, pots were selected for uniformity as far as possible and atypical examples were discarded. Spray solutions were applied with a Mardrive precision laboratory sprayer, calibrated to deliver 200 l/ha spray solution in a single pass. All replicate pots (3–5 per species per treatment) were sprayed with one pass of the sprayer.

After treatment, untreated control pots were placed at random among treated pots. Assessment of "% Phytotoxicity" was made by comparison with untreated controls on an arbitrary scale from 0 to 100%, where 0 means no visible effect and 100% means complete death. For any one assessment, all pots were rated by the same individual, assessments being performed "blind", without knowledge of the treatment. The bars in FIGS. 2, 3, 4, 10 and 11 show the averages of observations on the 3–5 replicates used.

Figure 5:
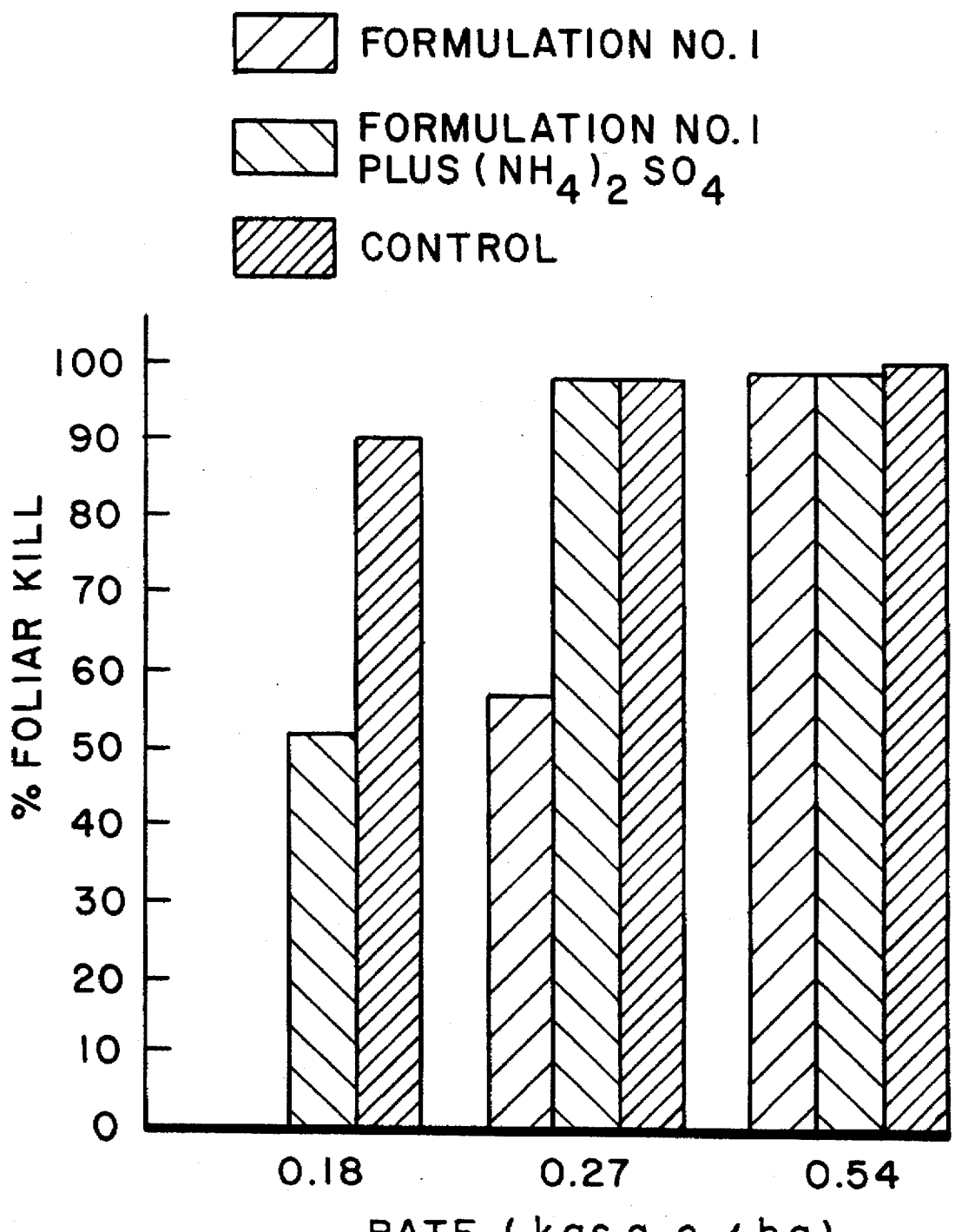
FIGS. 5 and 6 show results obtained in a field trial on various weeds in wheat stubble. As volunteer wheat, wheat is a weed in its own right. Also, its response to glyphosate is typical of that of a range of weed grasses.
Figure 6:
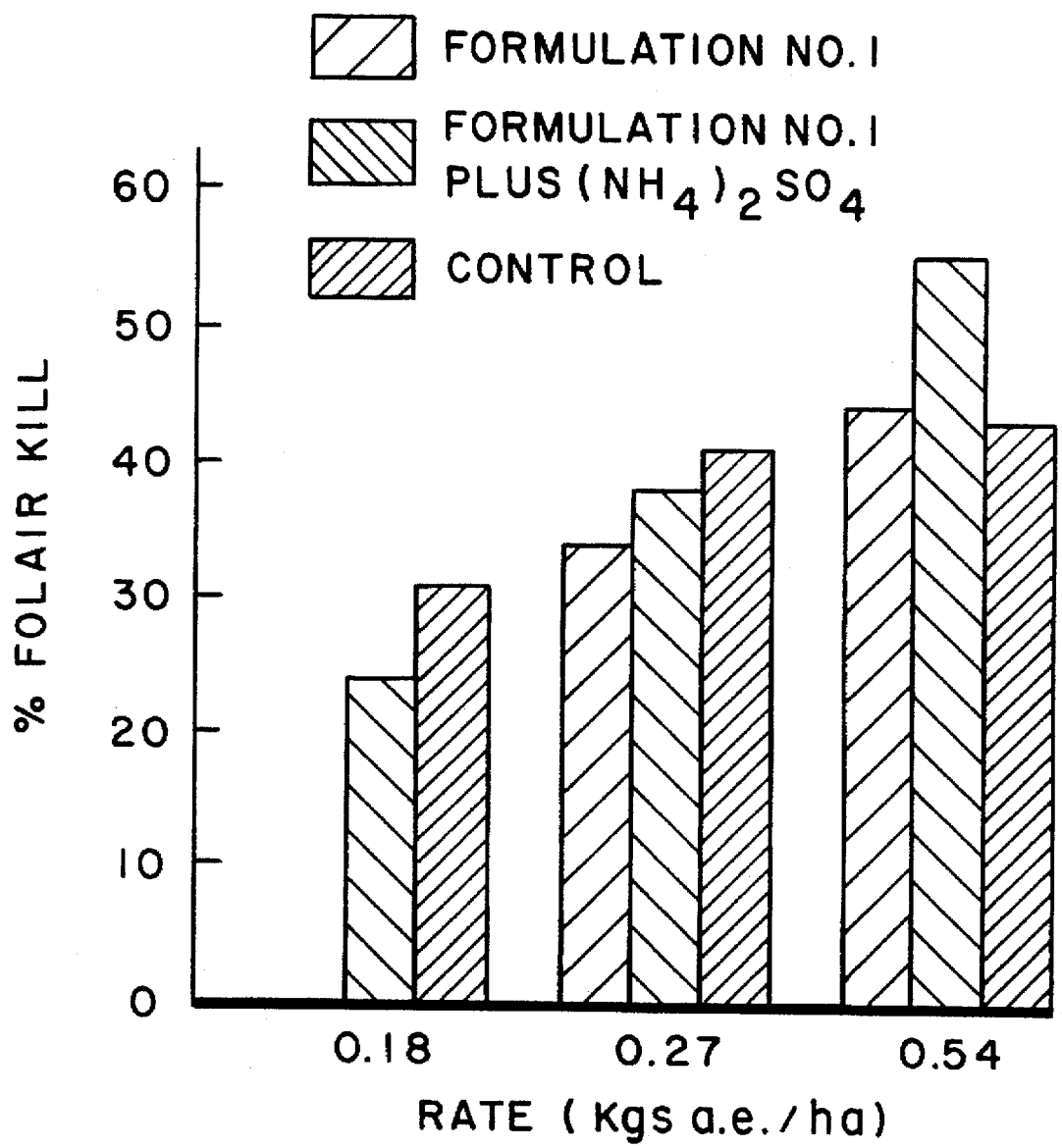

The trial which gave the results shown in FIGS. 5 and 6 was carried out in a field of wheat stubble which was 75% covered by weeds. About 35% of the weeds were volunteer wheat, and the remainder were a mixture of annual broadleaves, 35% chickweed (*Stellaria media*), 10% field pansy (*Viola arvensis*) and 10% scarlet pimpernel (*Anagallis arvensis*). At the time of spraying, the air temperature was 23° C., soil temperature 15° C., and relative humidity 48%, with zero wind velocity. The test design was a randomized complete block with four replicates and a unit plot size of 18m². The observations recorded are % foliage kill three weeks after treatment.

Figure 7:
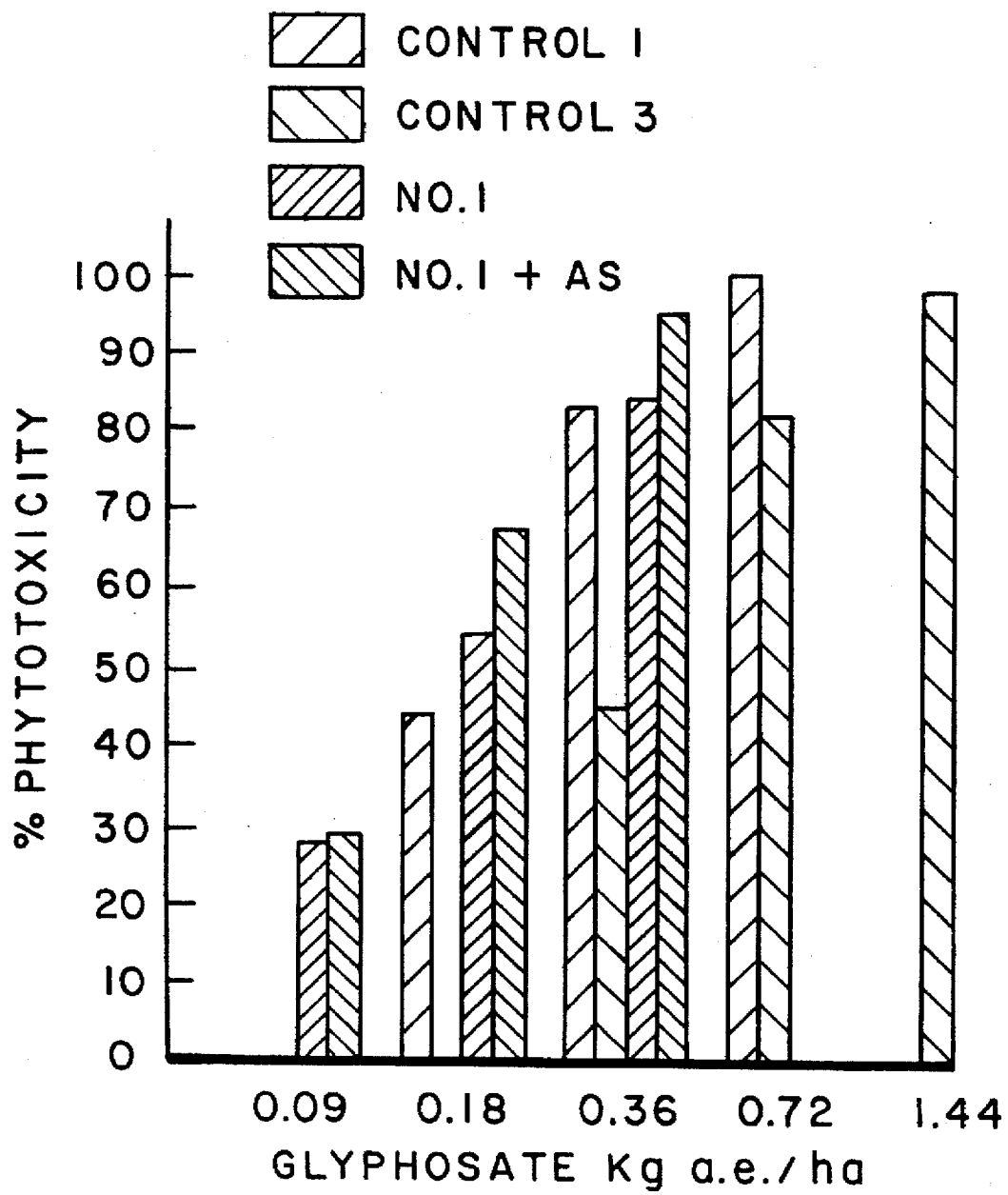
FIGS. 7 and 8 show results obtained in a field trial in sown pasture containing perennial ryegrass (*Lolium perenne*) and white clover (*Trifolium repens*)
Figure 8:
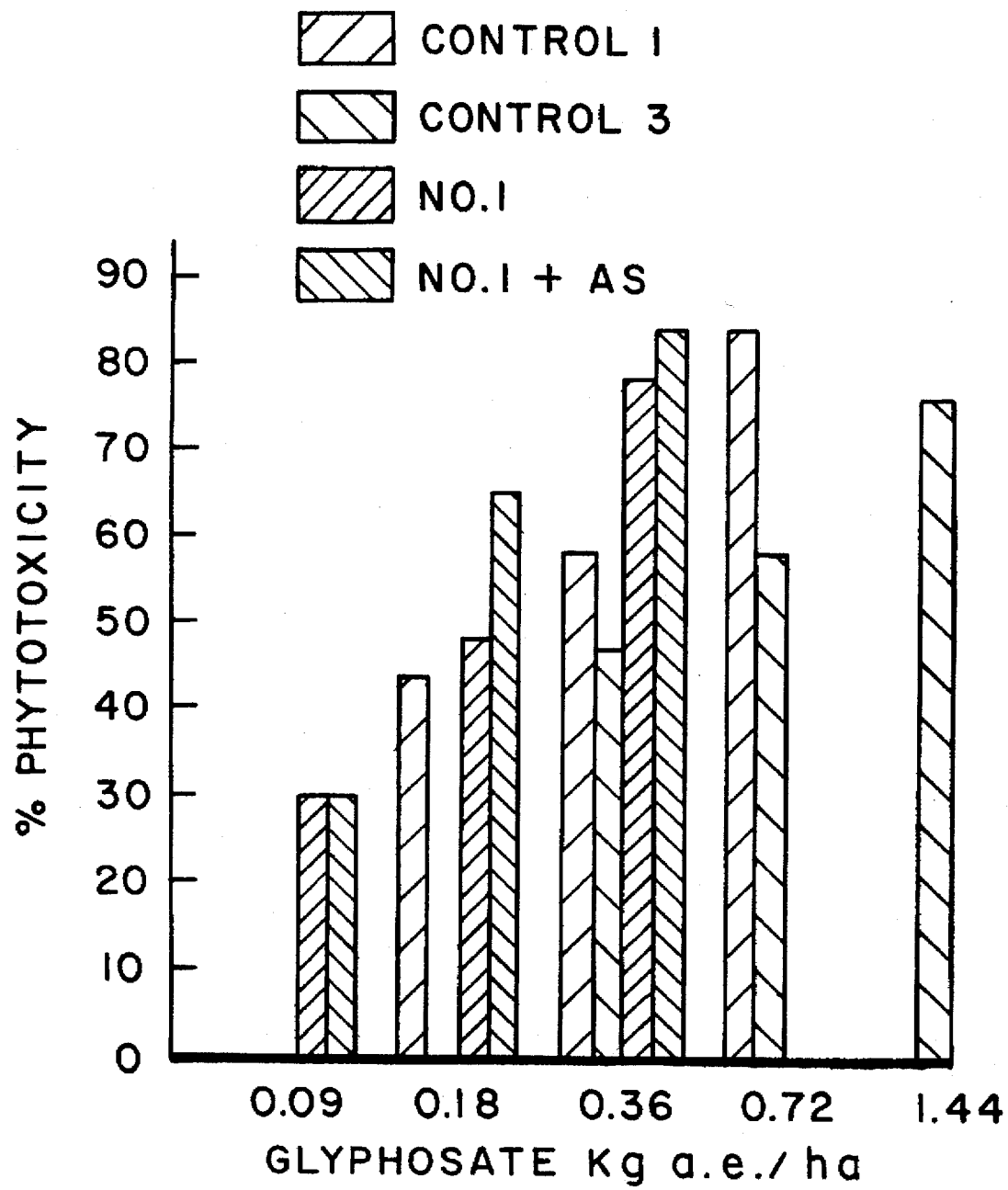

The trial which gave the results shown in FIGS. 7 and 8 was carried out in sown pasture containing in one part a pure stand of perennial ryegrass and in another part a mixture of various grasses and white clover. Data are shown for perennial ryegrass and white clover only. During spraying the air temperature was 18° C. and there was a slight to moderate wind. No rain fell for 2 days after spraying. The test design was a randomized complete block with three replicates of each treatment and twelve replicates of untreated plots. Plot size was 16m² in the perennial ryegrass sward plus 16m² in the mixed grass and clover sward. The observations recorded are % foliage kill 47 days after treatment.

Figure 9:
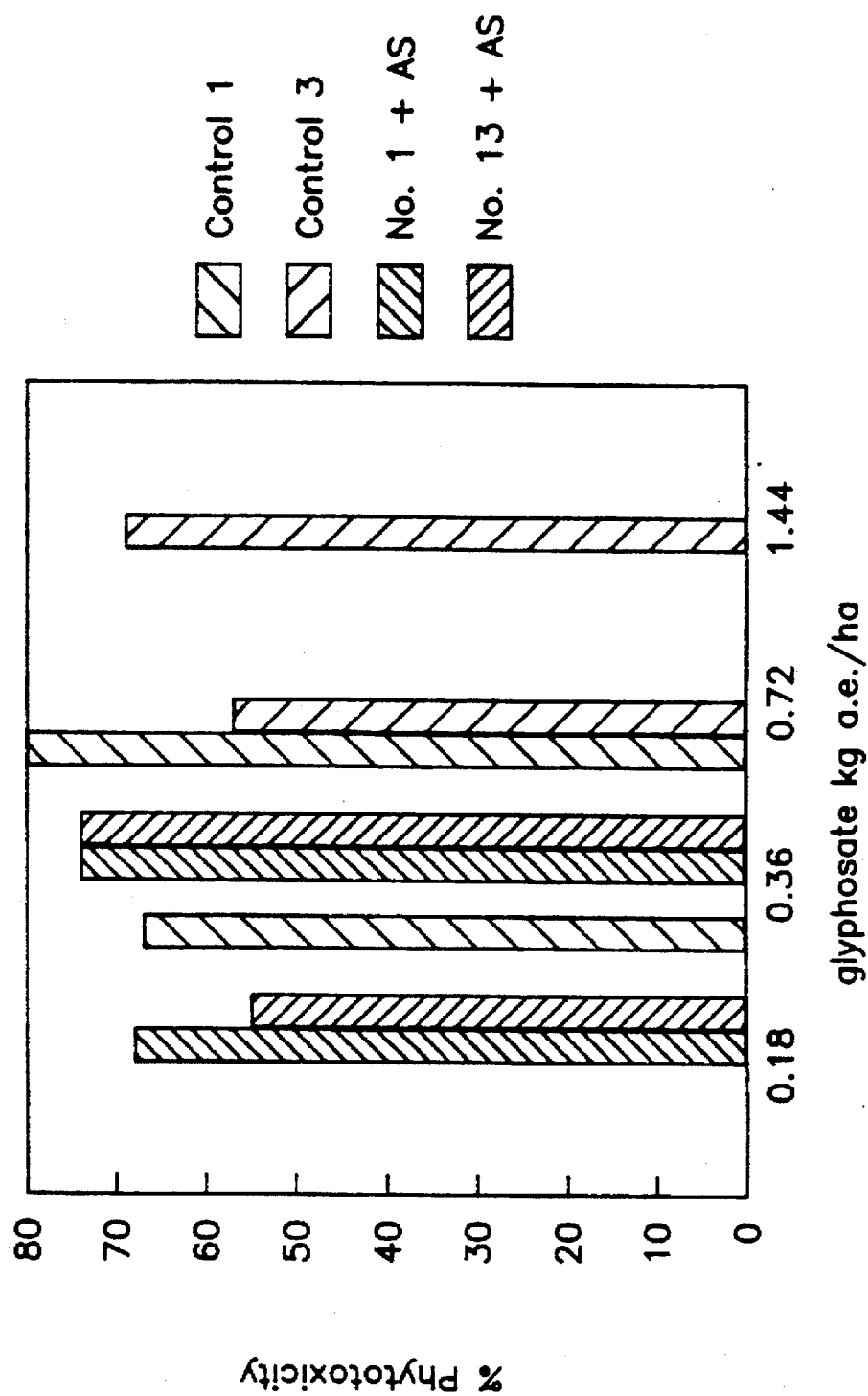
FIG. 9 shows results obtained on the perennial grass weed couch (*Elymus repens*) in cereal stubble.

The trial which gave the results shown in FIG. 9 was conducted in a field of cereal stubble carrying a moderate infestation of couch, fairly uniformly distributed over the trial area. During spraying the air temperature was 15° C. and there was a light to moderate wind. No rain fell for 5 days after spraying. The test design was a randomized complete block with three replicates and a plot size of 30m². The observations recorded are % foliage kill 25 days after treatment.

In preparing spray solutions, concentrates described in the Tables above were diluted with water so that at a spray volume equivalent to 200 l/ha, application rates in kg glyphosate a.e./ha were as indicated in FIGS. 1–11.

The spray solutions containing ammonium sulfate in the tests of FIG. 1 contained 6 parts by weight of ammonium sulfate per part by weight of glyphosate acid equivalent. The spray solutions containing ammonium sulfate used in the tests of FIGS. 2, 3 and 4 and in the field trial of FIGS. 5 and 6 contained 10 g/l of ammonium sulfate. In all these cases ammonium sulfate to glyphosate a.e. weight ratio exceeds 3.6:1 and the solutions containing ammonium sulfate are included as confirmation of prior art. The spray solutions containing ammonium sulfate in the field trials of FIGS. 7, 8 and 9 contained 3.6 parts by weight of ammonium sulfate per part by weight of glyphosate a.e. This is a lower ratio than disclosed in prior art.

The spray solutions used for comparative purposes (Controls) contained glyphosate wholly as the monoisopropylamine salt, and an ethoxylated tallowamine-based surfactant having an average of 15 ethoxy groups. In Control 1, the weight ratio was 2.94 parts of surfactant to 1 part of glyphosate a.e.; in Control 2 it was 2 parts of surfactant to 1 part of glyphosate a.e., and in Control 3 the weight ratio was 1 part of surfactant to 2 parts of glyphosate a.e. These ratios are similar to those in existing commercial formulations of glyphosate.

In the Figures, spray solutions are designated as "Formulations" and numbered according to the number of the solution in the Tables above from which they are derived.

FIG. 1 shows that on wheat, at all rates of application, herbicidal activity is at least as high for Formulation No. 1 of the invention with a 2:1 glyphosate a.e. to surfactant weight ratio and ammonium sulfate added as for Control 1, despite the presence in this Control of almost 6 times as much surfactant per unit of glyphosate a.e. as in Formulation 1. That Formulation 1 should perform as well as this in the presence of a large amount of added ammonium sulfate is surprising, but possibly could have been anticipated from prior art. However, what could not have been anticipated is the performance of Formulation 1 in the absence of ammonium sulfate. When compared with Control 3, which has the same glyphosate a.e. to surfactant ratio as Formulation No. 1 of the invention, Formulation No. 1 with no ammonium sulfate was as active at 0.18, 0.36 and 0.72 kg a.e./ha as Control 3 at twice these dosage rates, namely 0.36, 0.72 and 1.44 kg a.e./ha respectively. This is the reverse of what was expected based on prior art testing of compositions having similar surfactants but at much higher surfactant to glyphosate a.e. ratios.

Figure 2:
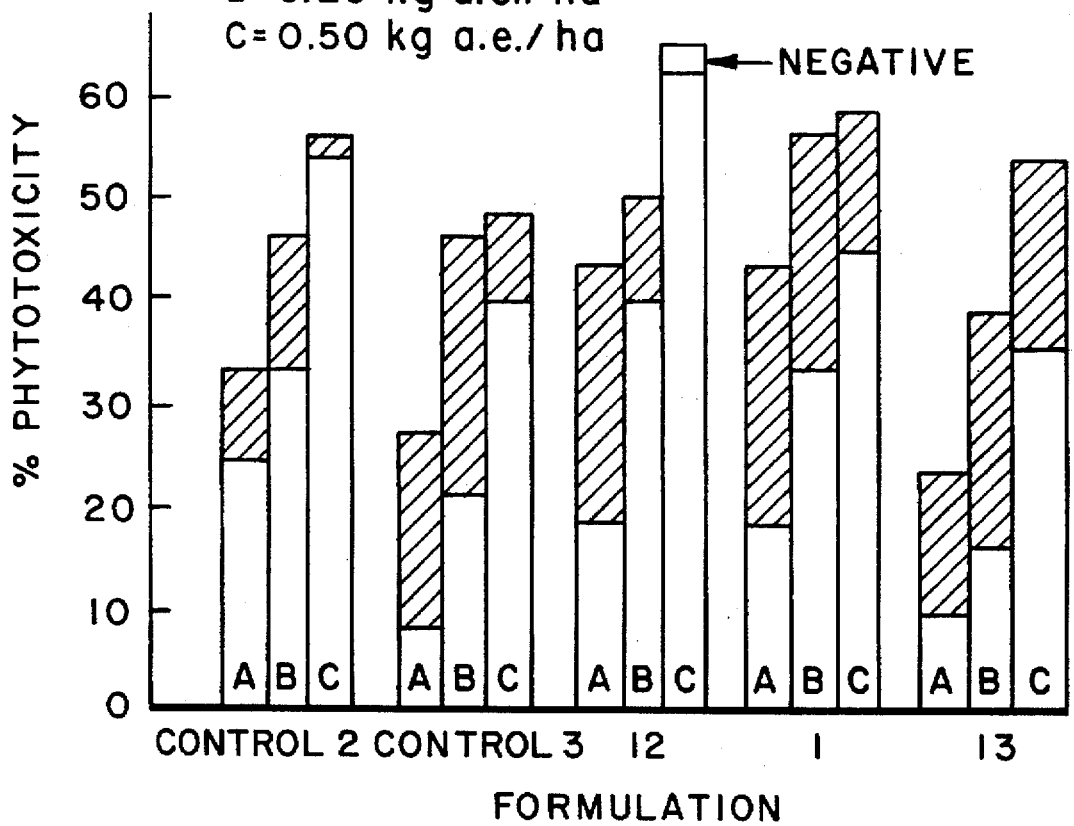
FIGS. 2, 3, 4 10 and 11 show results obtained in growth room tests on blackgrass (*Alopecurus myosuroides*)

FIG. 2 shows the results obtained 14 days after treatment with spray solutions containing C 2 as the surfactant on blackgrass. In the absence of ammonium sulfate, Formulation 12 (glyphosate a.e. to surfactant ratio 1:1) performed better than Control 2, which contains twice as much surfactant per unit weight of glyphosate. Formulation 1 (glyphosate a.e. to surfactant ratio 2:1) showed better activity than Control 3, which has the same glyphosate a.e. to surfactant ratio. Formulation 13 (glyphosate a.e. to surfactant ratio 4:1) had only slightly lower phytotoxicity than Control 3, despite the significantly lower level of surfactant relative to glyphosate in Formulation 13.

Figure 3:
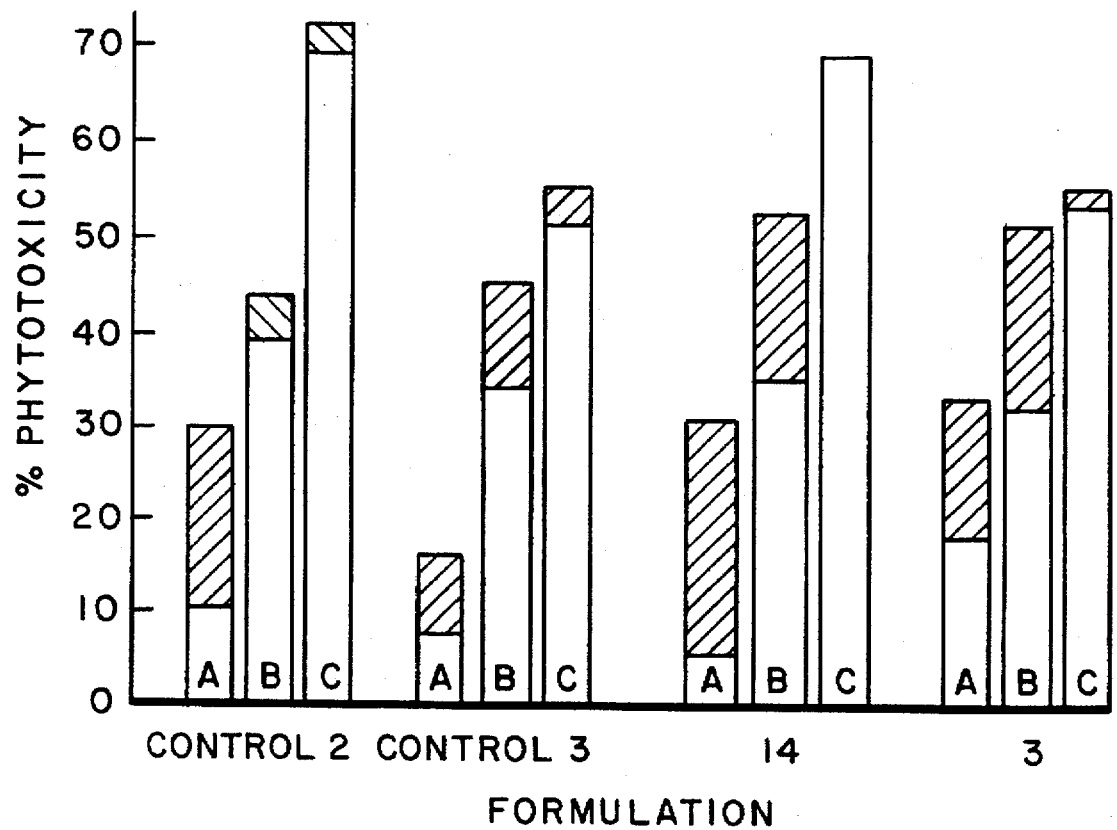

FIG. 3 shows the results obtained 14 days after treatment with spray solutions containing C 8 as the surfactant on blackgrass. In the absence of ammonium sulfate, Formulation 14 having a weight ratio of glyphosate a.e. to surfactant of 1:1 showed substantially the same activity at all dosage rates as Control 2 which has twice the level of surfactant. At the lowest rate of application, Formulation 3 (glyphosate a.e. to surfactant ratio 2:1) was significantly more active than Control 3 with the same level of surfactant.

Figure 4:
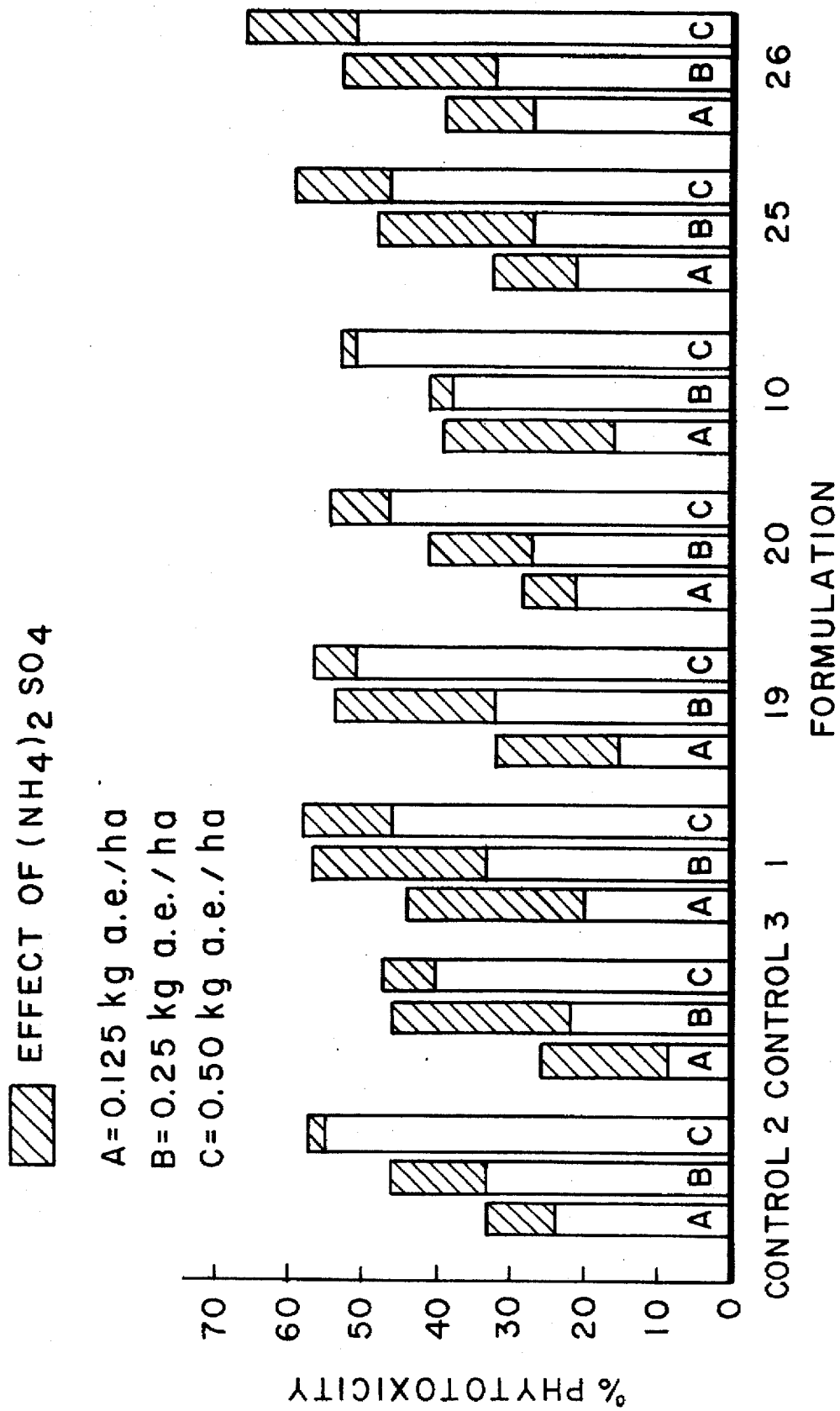

FIG. 4 shows results obtained 14 days after treatment with formulations containing monoisopropylamine glyphosate (1 and 10), ammonium glyphosate (20 and 26) and potassium glyphosate (19 and 25). All the formulations have a glyphosate a.e. to surfactant weight ratio of 2:1, the same as Control 3. The generally enhanced herbicidal activity of the formulations relative to this Control is clear both with and without ammonium sulfate added, and in some instances the formulations with ammonium sulfate added have phytotoxicities at least as high as Control 2 which has four times the level of surfactant.

FIG. 5 shows confirmation in the field of growth room results that on volunteer wheat at 0.27 kg a.e./ha, the performance of Formulation No. 1 is enhanced by the addition of ammonium sulfate to a level at which the performance is substantially the same as that of Control 1, despite a much lower surfactant to glyphosate a.e. ratio. At 0.54 kg a.e./ha the addition of ammonium sulfate had virtually no effect on the performance of Formulation No. 1. With or without ammonium sulfate, it was substantially the same as the Control with almost six times the level of surfactant.

FIG. 6 shows the herbicidal effect of glyphosate formulations on annual broadleaves. Formulation 1 of the invention is at least equivalent to Control 1 at 0.54 kg a.e./ha despite having an almost six times lower surfactant level.

FIGS. 7 and 8 show the herbicidal effect of Formulation No. 1. on perennial ryegrass and white clover. On both species the formulation of the invention was equal or superior in activity to Control 1, despite its much lower surfactant level, and showed activity equal or superior to that of Control 3 having the same surfactant level but applied at twice the dosage rate. Addition of ammonium sulfate at a weight ratio to glyphosate a.e. close to the upper limit of the range claimed herein gave only a slight further increase in the activity of Formulation No. 1.

FIG. 9 shows the herbicidal effect of formulations of the invention on couch. Both Formulation No. 1 and No. 13, with the addition of ammonium sulfate at a 3.6:1 weight ratio to glyphosate a.e., were more active than Control 1 which contains almost six times as much surfactant per unit of glyphosate a.e. as Formulation 1 and almost 12 times as much as Formulation No. 13. Both formulations of the invention at 0.18 and 0.36 kg a.e./ha were equal to Control 3 applied at four times these dosage rates, namely 0.72 and 1.44 kg a.e./ha respectively.

Figure 10:
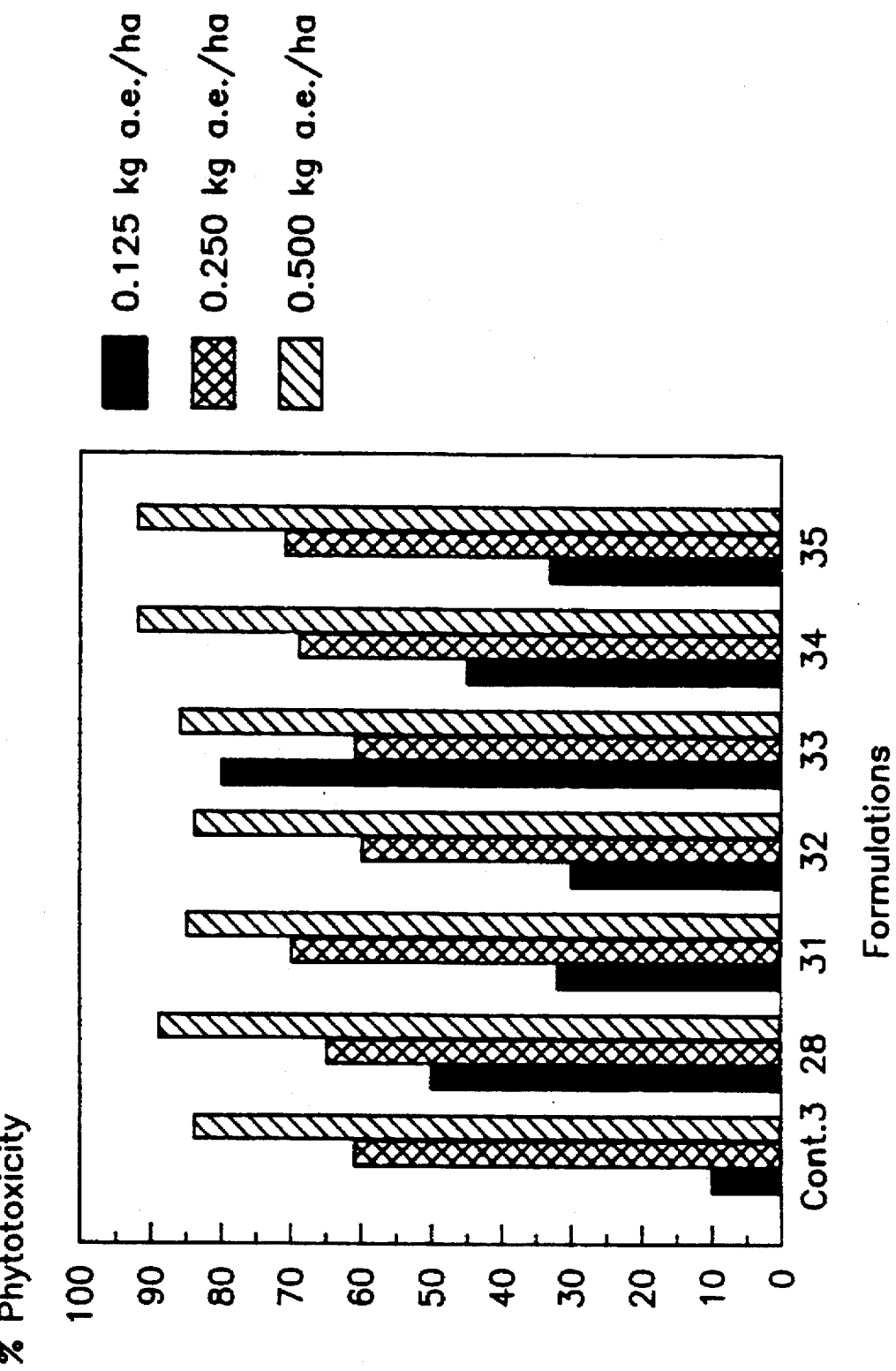

FIG. 10 shows results obtained 22 days after treatment with spray solutions prepared by the dilution of concentrates containing various surfactants and glyphosate derived wholly from the isopropylamine salt. In all solutions, glyphosate and surfactant were present in the ratio 2:1. At the lowest rate of application, all solutions of the invention were more active than the control. At 0.25 kg glyphosate a.e./ha, all solutions except those having C 10 or C 8 as the surfactant were more active than the Control.

Figure 11:
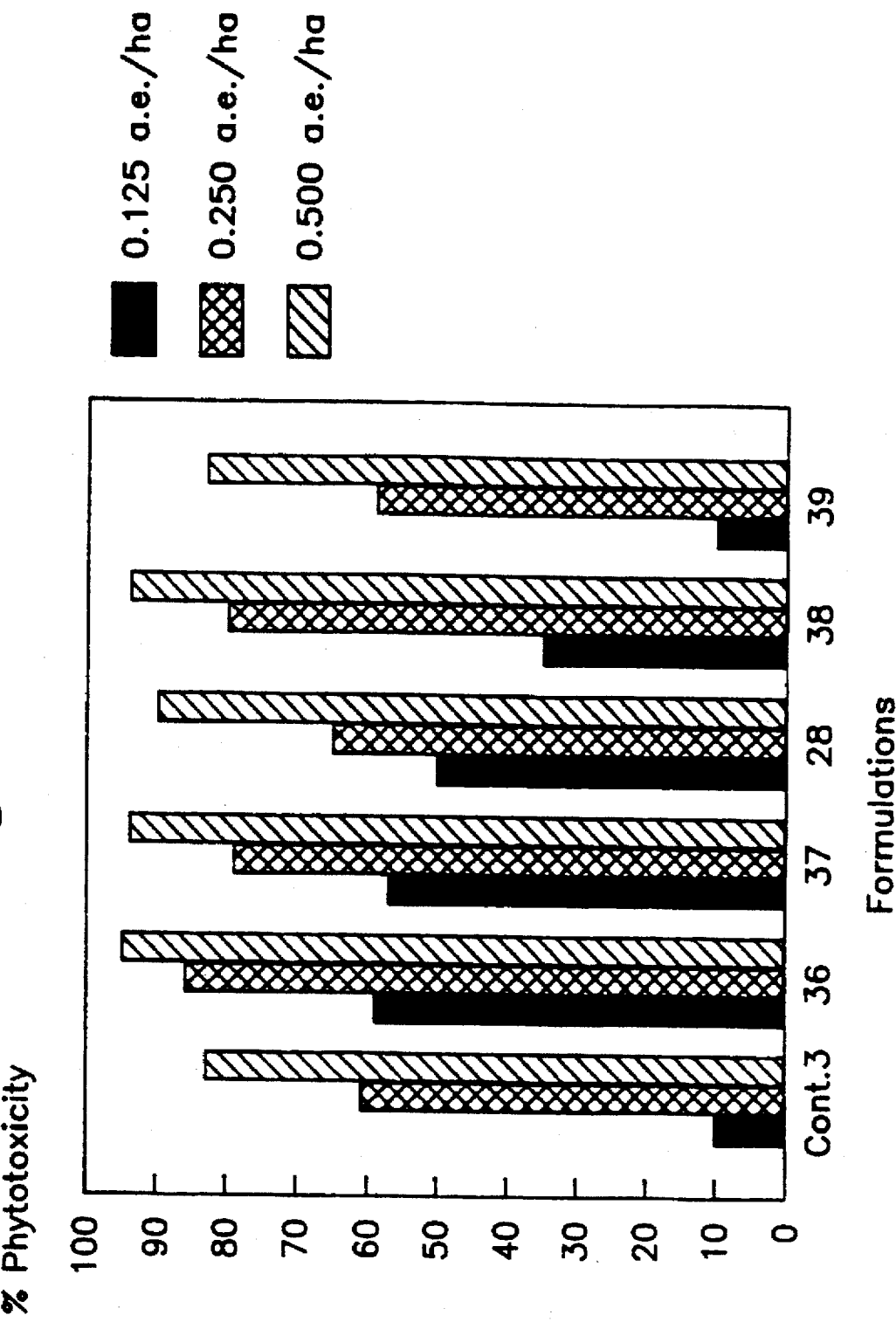

FIG. 11 shows the results obtained 22 days after treatment using a series of spray solutions containing C 2 as the surfactant and with decreasing proportions of surfactant. The glyphosate in these solutions is derived wholly from the monoisopropylamine salt. Decrease in activity occurs as the proportion of surfactant decreases, but at the lowest rate of application the solution of the invention (from Formulation 38) containing glyphosate a.e. and surfactant in the ratio 4:1 was over twice as active as the Control containing twice as much surfactant. At the higher rates of application it was at least as active as the Control.

We claim:

1. A herbicidal composition which comprises a concentrated aqueous solution containing
   (a) solubilized glyphosate in amount equivalent to at least 40 grams per liter of glyphosate acid,
   (b) a surfactant which is (i) an amine having the formula

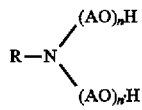

where R represents a straight- or branched-chain alkyl or alkenyl group having from about 8 to about 22 carbon atoms, A represents an alkylene group, and n and n' are integers such that n+n' has a value of from about 2 to about 8, (ii) a mixture of such amines having different groups R, the average number of carbon atoms in the groups R being from about 8 to about 22, or (iii) a mixture of such amines having different values of n and n', n and n' being integers such that in the mixture the average value of n+n' is from about 2 to about 8, R having a single value or an average value as in a mixture (ii);
and optionally (c) an agriculturally acceptable inorganic ammonium salt;
wherein the weight ratio of (a) expressed as glyphosate acid equivalent to (b) is from about 1:1.75 to about 6:1 and wherein the weight ratio of (c) to (a) expressed as glyphosate acid equivalent is at most about 3.6:1 said solution adapted for dilution and application to plants at a rate of from about 100 to about 400 liters per hectare.

2. A composition according to claim 1 wherein the weight ratio of component (a) expressed as glyphosate acid equivalent to surfactant is from about 1:1 to about 4:1.

3. A composition according to claim 2 wherein the weight ratio of component (a) expressed as glyphosate acid equivalent to surfactant is from about 1.5:1 to about 3:1.

4. A composition according to claims 1, 2 or 3 in which A in the formula of the surfactant represents an ethylene or propylene group and the surfactant is a mixture in which n+n' has an average value of from about 2 to about 8.

5. A composition according to claim 4 in which A represents an ethylene group.

6. A composition according to claim 5 wherein the number or average number of carbon atoms in R is from about 8 to about 18.

7. A composition according to claim 6 wherein the surfactant is an ethoxylated derivative of cocoamine, tallowamine or oleylamine where n+n' has an average value of about 2, about 5 or about 8.

8. A composition according to any of claims 1–3 or 5–7 wherein the glyphosate is present (i) partly as glyphosate acid solubilized by means of the surfactant (b) and partly as a salt of glyphosate with an agriculturally-acceptable cation other than the cationic form of the surfactant, or (ii) wholly as glyphosate acid solubilized by the surfactant.

9. A composition according to claim 8 wherein the amount of surfactant is at least 90% of the 1:1 molar equivalent of the glyphosate acid.

10. A composition according to claim 9 wherein the salt of glyphosate in addition to that formed with the cationic form of the surfactant is the isopropylamine, ammonium or potassium salt.

11. A composition according to claim 1 containing from about 90 to about 450 grams per liter of component (a) expressed as glyphosate acid equivalent, said composition being substantially free of inorganic ammonium salt.

12. A composition according to claim 1 consisting essentially of an aqueous solution containing from about 340 to about 420 grams per liter of component (a) expressed as glyphosate acid equivalent and wherein the salt of glyphosate is the monoisopropylamine salt, the surfactant is an ethoxylated cocoamine derivative with n+n' having an average value of about 2, and the weight ratio of (a) to (b) is about 2:1.

13. A composition according to claim 1 which comprises an aqueous solution containing an agriculturally acceptable inorganic ammonium salt in addition to components (a) and (b).

14. A composition according to claim 13 which contains from about 80 to about 150 grams per liter of component (a) expressed as glyphosate acid equivalent and from about 100 to about 350 grams per liter of inorganic ammonium salt.

15. A composition according to claims 13 or 14 wherein the inorganic ammonium salt is ammonium sulfate.

16. A composition according to claim 14 which contains from about 100 to about 130 grams per liter of component (a) expressed as glyphosate acid equivalent, from about 100 to about 180 grams per liter of component (b), component (a) being the isopropylamine salt of glyphosate and component (b) being an ethoxylated cocoamine derivative with n+n' having an average value of about 2, and from about 260 to about 320 grams per liter of ammonium sulfate.

17. A herbicidal method which comprises spraying weeds with a spray solution at from about 100 to about 400 liters of solution per hectare, said solution containing
   (a) solubilized glyphosate;
   (b) a surfactant which is (i) an amine having the formula

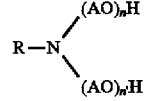

where R represents a straight- or branched-chain alkyl or alkenyl group having from about 8 to about 22 carbon atoms, A represents an alkylene group, and n and n' are integers such that n+n' has a value of from about 2 to about 8, (ii) a mixture of such amines having different groups R, the average number of carbon atoms in the groups R being from about 8 to about 22, or (iii) a mixture of such amines having different values of n and n', n and n' being integers such that in the mixture the average value of n+n' is from about 2 to about 8, R having a single value or an average value as in a mixture (ii);
and optionally (c) an agriculturally acceptable inorganic ammonium salt;

the weight ratio of (a) expressed as glyphosate acid equivalent to (b) in the spray solution being from about 1:1.75 to about 6:1, and the concentration of (a) in the spray solution being such that the application rate of glyphosate acid equivalent is from about 0.125 kg to about 1.5 kg per hectare;

and the weight ratio of (c) to (a) expressed as glyphosate acid equivalent being at most about 3.6:1.

18. A method according to claim 17 in which the agriculturally-acceptable inorganic ammonium salt is ammonium sulfate.

19. A method according to claim 17 in which the spray solution is substantially free of inorganic ammonium salt.

20. A method according to claim 17 in which the spray solution is prepared by mixing a composition according to claim 11 with water and with an agriculturally acceptable inorganic ammonium salt.

21. A method according to claim 20 in which the inorganic ammonium salt is ammonium sulfate.

* * * * *